US007063955B2

(12) United States Patent
Cheng et al.

(10) Patent No.: US 7,063,955 B2
(45) Date of Patent: Jun. 20, 2006

(54) METHOD FOR PRODUCTION OF ASYMMETRIC CAROTENOIDS

(75) Inventors: Qiong Cheng, Wilmington, DE (US); Luan Tao, Claymont, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 684 days.

(21) Appl. No.: 10/292,577

(22) Filed: Nov. 12, 2002

(65) Prior Publication Data

US 2003/0143660 A1    Jul. 31, 2003

Related U.S. Application Data

(60) Provisional application No. 60/331,830, filed on Nov. 20, 2001.

(51) Int. Cl.
C12P 23/00 (2006.01)
C12N 9/02 (2006.01)
C12N 1/19 (2006.01)
C12N 1/21 (2006.01)
C07H 21/04 (2006.01)

(52) U.S. Cl. .......... 435/67; 435/143; 435/183; 435/189; 435/252.3; 435/252.33; 435/254.11; 435/410; 536/23.2

(58) Field of Classification Search .......... 435/67, 435/183, 189, 252.3, 252.33, 410, 143; 536/23.2
See application file for complete search history.

(56) References Cited

U.S. PATENT DOCUMENTS

| 5,429,939 | A | 7/1995 | Misawa et al. |
| 5,530,188 | A | 6/1996 | Ausich et al. |
| 5,530,189 | A | 6/1996 | Ausich et al. |
| 5,545,816 | A | 8/1996 | Ausich et al. |
| 5,656,472 | A | 8/1997 | Ausich et al. |
| 5,744,341 | A | 4/1998 | Cunningham, Jr. et al. |
| 5,792,903 | A | 8/1998 | Hirschberg et al. |
| 2003/0170847 | A1* | 9/2003 | Bramucci et al. ........... 435/193 |

FOREIGN PATENT DOCUMENTS

| WO | WO 01/66703 A1 | 9/2001 |
| WO | WO 02/41833 A2 | 5/2002 |
| WO | WO 02/079395 A2 | 10/2002 |

OTHER PUBLICATIONS

Tao et al. (2004) Mol. Gen. Genomics vol. 271, pp. 180-188.*
Armstrong. G., Comprehensive Natural Products Chemistry, Elsevier Press, Carotenoid Genetics and Biochemistry, vol. 2, pp. 321-352, 1999.
Cunningham et al., Functional Analysis of the β and ε Lycopene Cyclase Enzymes of *Arabidopsis* Reveals a Mechanism for Control of Cyclic Carotenoid Formation, Plant Cell, 8: 1613-1626, 1996.
Cunningham et al., One ring or two? Determination of ring number in carotenoids by lycopene ε-cyclases, PNAS, 98: 2905-2910, 2000.
Schnurr et al., Expression, purification and properties of lycopene cyclase from *Erwinia uredovora*, Biochem J. 315: 869-874, 1996.
An et al., Monocyclic Carotenoid Biosynthetic Pathway in the Yeast *Phaffia rhodozyma* (*Xanthophyllomyces dendrorhous*), J. Biosci. Bioeng. 88(2), 189-193, 1999.
Armstrong et al., Eubacteria Show Their True Colors: Genetics of Carotenoid Pigment Biosynthesis from Microbes to Plants, J. Bact. 176: 4795-4802, 1994.
Armstrong, Genetics of Eubacterial Carotenoid Biosynthesis: A Colorful Tale, Annu. Rev. Microbiol, 51: 629-659, 1997.
Ichiyama et al., Carotenoid Pigments of Genus *Rhodococcus*, Microbiol. Immunol. 33: 503-508, 1989.
Mergaert et al., Transfer of *Erwinia ananas* and *Erwinia stewartii* to the Genus *Pantoea* emend. As *Pantoea ananas* comb. Nov. and *Pantoea stewartii* comb. Nov., Respectively, and Description of *Pantoea stewartii* subsp. Indologenes subsp. nov., Int. J. Syst. Bacteriol. 43: 162-173, 1993.
Cunningham et al., Molecular Structure and Enzymatic Function of Lycopene Cyclase from the Cyanobacterium *synechococcus* sp Strain PCC7942, Plant Cell. 6: 1107-1121.

(Continued)

Primary Examiner—Elizabeth Slobodyansky

(57) ABSTRACT

Genes have been isolated from *Rhodococcus* and *Deinococcus* which encode a specific lycopene β-cyclase capable of converting acyclic carotenoids with at least one ψ-end group to the corresponding asymmetric carotenoid containing a single β-ionone ring end group. The genes are new. Transformed host cells expressing the present genes and methods for the bio-conversion of acylic carotenoid substrates to corresponding asymmetric carotenoid are also provided.

1 Claim, 4 Drawing Sheets

OTHER PUBLICATIONS

Hugueney et al., Metabolism of cyclic carotenoids: a model for the alteration of this biosynthetic pathway in *Capsicum annuum* chromoplasts, Plant J. 8: 417-424, 1995.

Database GenBank, US National Libraryu of Medicine (Bethesda, MD USA) Accession No.: AAF 10377, "lycopene cyclase [*Deinococcus radiodurans*]", White et al., Nov. 22, 1999.

* cited by examiner

METHOD FOR PRODUCTION OF ASYMMETRIC CAROTENOIDS

This application claims the benefit of U.S. Provisional Application No. 60/331,830, filed Nov. 20, 2001.

FIELD OF THE INVENTION

This invention is in the field of microbiology. More specifically, this invention pertains to methods for the microbial production of monocyclic carotenoids.

BACKGROUND OF THE INVENTION

Carotenoids are pigments that are ubiquitous throughout nature and synthesized by all oxygen evolving photosynthetic organisms, and in some heterotrophic growing bacteria and fungi. Carotenoids provide color for flowers, vegetables, insects, fish and birds. Colors of carotenoid range from yellow to red with variations of brown and purple. As precursors of vitamin A, carotenoids are fundamental components in human diet, playing an important role in human health. Industrial uses of carotenoids include pharmaceuticals, food supplements, animal feed additives and colorants in cosmetics to mention a few.

Because animals are unable to synthesize carotenoid de novo, they must obtain them by dietary means. Thus, manipulation of carotenoid production and composition in plants or bacteria can provide new or improved source for carotenoids.

Carotenoids come in many different forms and chemical structures. Most naturally occurring carotenoids are hydrophobic tetraterpenoids containing a $C_{40}$ methyl-branched hydrocarbon backbone derived from successive condensation of eight $C_5$ isoprene units (IPP). In addition, novel carotenoids with longer or shorter backbones occur in some species of nonphotosynthetic bacteria. The term "carotenoid" includes both carotenes and xanthophylls. A "carotene" refers to a hydrocarbon carotenoid. Carotene derivatives that contain one or more oxygen atoms, in the form of hydroxy-, methoxy-, oxo-, epoxy-, carboxy-, or aldehydic functional groups, or within glycosides, glycoside esters, or sulfates, are collectively known as "xanthophylls". Carotenoids are furthermore described as being acyclic, monocyclic, or bicyclic depending on whether the ends of the hydrocarbon backbones have been cyclized to yield aliphatic or cyclic ring structures (Armstrong, G., *Comprehensive Natural Products Chemistry*, Elsevier Press, volume 2, pp. 321–352. (1999)).

Carotenoid biosynthesis starts with the isoprenoid pathway to generate the $C_5$ isoprene unit, isopentenyl pyrophosphate (IPP). IPP was condensed with its isomer dimethylallyl pyrophophate (DMAPP) to $C_{10}$ geranyl pyrophosphate (GPP) and elongated to $C_{15}$ farnesyl pyrophosphate (FPP). FPP synthesis is common in both carotenogenic and non-carotenogenic bacteria. Subsequent enzymes in the carotenoid pathway generate carotenoid pigments from the FPP precursor and can be divided into two categories: carotene backbone synthesis enzymes and subsequent modification enzymes. The backbone synthesis enzymes include geranyl geranyl pyrophosphate synthase (CrtE), phytoene synthase (CrtB), phytoene dehydrogenase (CrtI) and lycopene cyclase (CrtY/L), etc. The modification enzymes include ketolases, hydroxylases, dehydratases, glycosylases, etc.

Lycopene cyclases are a class of enzymes responsible for catalyzing the formation of cyclical carotenoids from lycopene (ψ,ψ-carotene), an acyclic symmetrical carotenoid. Lycopene cyclases catalyze the formation of ionone rings from the ψ end groups found on lycopene (FIG. 1).

Two types of lycopene cyclases (β-cyclases and ε-cyclases) have been reported (Cunningham et al., *Plant Cell.* 8:1613–1626 (1996)). All previously described lycopene β-cyclases catalyze the formation of β-ionone rings from ψ end groups found on acyclic carotenoids such as lycopene (ψ,ψ-carotene), usually resulting in a symmetrical bicyclic product such as β-carotene. The lycopene ε-cyclases, usually found in plants, catalyze the formation of ε-ionone rings from the ψ end groups. Most lycopene ε-cyclases catalyze formation of the asymmetric monocyclic δ-carotene (ψ,ε-carotene). A lycopene ε-cyclase from lettuce catalyzes the formation of bicyclic ε-carotene (ε,ε-carotene) (Cunningham et al., *PNAS*, 98:2905–2910, (2000)). The difference between the β-ionone and ε-ionone ring structure is based on the location of the double bond within the 6-member ring.

The known lycopene β-cyclases function symmetrically on lycopene, creating symmetric bicyclic β-carotene through a monocyclic γ-carotene intermediate. A lycopene β-cyclase isolated from *Pantoea ananatis* was reported to produce bicyclic β-carotene via a 2-step reaction involving γ-carotene as the intermediate (Schnurr et al., *Biochem J.* 315: 869–874 (1996)).

Monocyclic carotenoids are sometimes present as part of the mixture during bicyclic carotenoids synthesis. Certain methods such as using a β-cyclase mutant with decreased activity or a partial inhibition of the β-cyclase could be used to enrich for the monocyclic carotenoids in the mixture. Isolation and purification of monocyclic carotenoids from the mixture of carotenoids derived from β-cyclases often requires a significant investment in time and resources. No prokaryotic lycopene β-cyclase has been proven to selectively produce only monocyclic carotenoids.

A monocyclic β-cyclase pathway has been proposed to exist in the yeast *Phaffia rhodozyma* by enzyme inhibition experiments (An et al., *J. Biosci. Bioeng.* 88(2): 189–193 (1999)). However, the monocyclic carotenoids produced in *Phaffia* were a minor component (<20%) of the total carotenoid mixture, and the presence of an enzyme that was selective for the production of monocyclic carotenoids was not taught.

Plant lycopene ε-cyclases have been shown to primarily make monocyclic carotenoids, and only make ε-ionone ring structures (Cunningham et al., *Plant Cell.* 8:1613–1626 (1996) and Cunningham F. and Sun Z. U.S. Pat. No. 5,744,341).

The genetics of carotenoid pigment biosynthesis are well known (Armstrong et al., *J. Bact.* 176: 4795–4802 (1994); *Annu. Rev. Microbiol.* 51:629–659 (1997)). This pathway is extremely well studied in the Gram-negative, pigmented bacteria of the genera Pantoea, formerly known as *Erwinia*. In both *E. herbicola* EHO-10 (ATCC 39368) and *E. uredovora* 20D3 (ATCC 19321), the crt genes are clustered in two operons, crt Z and crtEXYIB (U.S. Pat. No. 5,656,472; U.S. Pat. No. 5,545,816; U.S. Pat. No. 5,530,189; U.S. Pat. No. 5,530,188; U.S. Pat. No. 5,429,939). Despite the similarity in operon structure, the DNA sequences of *E. uredovora* and *E. herbicola* crt genes show no homology by DNA-DNA hybridization (U.S. Pat. No. 5,429,939).

Although the genes involved in carotenoid biosynthesis pathway are known in some organisms, genes involved in carotenoid biosynthesis in *Rhodococcus* and *Deinococcus* bacteria are not described in the existing literature. Analytical characterization of carotenoid pigments from several strains of *Rhodococcus* was conducted (Ichiyama et al., *Microbiol. Immunol.* 33:503–508 (1989)). However, the analytical characterization did not attempt to characterize the enzymes responsible for the "γ-carotenoid-like" compounds reported.

The problem to be solved therefore is to provide methods and materials useful for the selective production of asymmetric carotenoids containing a single β-ionone ring. Applicants have solved the stated problem by isolating and characterizing genes encoding for a novel lycopene β-cyclase (crtL), isolated from both *Rhodococcus* and *Deinococcus*, which encode polypeptides that selectively produces monocyclic (β-ionone ring) carotenoids without significant bicyclic carotenoid synthesis.

SUMMARY OF THE INVENTION

The present invention provides a method for the production of asymmetric carotenoid compounds comprising:
a) providing a host cell which produces acyclic carotenoids with at least one ψ-end group wherein said host cell expresses a lycopene β-cyclase selected from the group consisting of:
  (i) an isolated nucleic acid molecule encoding the amino acid sequence selected from the group consisting of SEQ ID NO:2 and SEQ ID NO:4;
  (ii) an isolated nucleic acid molecule that hybridizes with (i) under the following hybridization conditions: 0.1×SSC, 0.1% SDS, 65° C. and washed with 2×SSC, 0.1% SDS followed by 0.1×SSC, 0.1% SDS; and
  (iii) an isolated nucleic acid molecule that encodes a polypeptide having at least 70% identity to the polypeptides selected from the group consisting of SEQ ID NO:2 and SEQ ID NO:4, based on the Smith-Waterman method of alignment;
b) growing the host cell of (a) under conditions whereby asymmetric carotenoids are produced; and
c) Optionally recovering said asymmetric carotenoids.

In a preferred embodiment the host cell of the invention comprises; at least one copy of a gene encoding a geranylgeranyl pyrophosphate synthase enzyme; at least one copy of a gene encoding a phytoene synthase enzyme; and at least one copy of a gene encoding a phytoene dehydrogenase enzyme.

In an alternate embodiment the acyclic carotenoid may be added exogenousely to the biocatalyst. Accordingly the invention provides a method for the production of asymmetric carotenoid compounds comprising:
a) providing a host cell wherein said host cell expresses a lycopene β-cyclase selected from the group consisting of:
  (i) an isolated nucleic acid molecule encoding the amino acid sequence selected from the group consisting of SEQ ID NO:2 and SEQ ID NO:4;
  (ii) an isolated nucleic acid molecule that hybridizes with (i) under the following hybridization conditions: 0.1×SSC, 0.1% SDS, 65° C. and washed with 2×SSC, 0.1% SDS followed by 0.1×SSC, 0.1% SDS; and
  (iii) an isolated nucleic acid molecule that encodes a polypeptide having at least 70% identity to the polypeptides selected from the group consisting of SEQ ID NO:2 and SEQ ID NO:4 based on the Smith-Waterman method of alignment;
b) contacting the host cell of (a) with an acyclic carotenoid comprising least one ψ-end group;
c) growing the host cell of (b) under conditions whereby asymmetric carotenoids are produced; and
d) optionally recovering said asymmetric carotenoids.

Additionally the invention provides a method of regulating asymmetric carotenoid biosynthesis in an organism comprising:
(a) providing a host cell which produces acyclic carotenoids with at least one ψ-end group;
(b) introducing into the host cell of (a) a lycopene β-cyclase gene selected from the group consisting of:
  (i) an isolated nucleic acid molecule encoding the amino acid sequence selected from the group consisting of SEQ ID NO:2 and SEQ ID NO:4;
  (ii) an isolated nucleic acid molecule that hybridizes with (i) under the following hybridization conditions: 0.1×SSC, 0.1% SDS, 65° C. and washed with 2×SSC, 0.1% SDS followed by 0.1×SSC, 0.1% SDS; and
  (iii) an isolated nucleic acid molecule that encodes a polypeptide having at least 70% identity to the polypeptides selected from the group consisting of SEQ ID NO:2 and SEQ ID NO:4, based on the Smith-Waterman method of alignment;
(c) growing the host cell of (b) under conditions whereby the lycopene β-cyclase gene is expressed and asymmetric carotenoid biosynthesis is regulated.

Additionally the invention provides a method for the identification of a gene encoding a lycopene β-cyclase which catalyzes the production of asymmetric carotenoids from acyclic carotenoids having at least one ψ-end group comprising:
(a) probing a genomic library with a portion of a nucleic acid molecule selected from the group consisting of:
  (i) an isolated nucleic acid molecule encoding the amino acid sequence selected from the group consisting of SEQ ID NO:2 and SEQ ID NO:4,
  (ii) an isolated nucleic acid molecule that hybridizes with (i) under the following hybridization conditions: 0.1×SSC, 0.1% SDS, 65° C. and washed with 2×SSC, 0.1% SDS followed by 0.1×SSC, 0.1% SDS; and
  (iii) an isolated nucleic acid molecule that encodes a polypeptide having at least 70% identity to the polypeptides selected from the group consisting of SEQ ID NO:2 and SEQ ID NO:4 based on the Smith-Waterman method of alignment;
(b) identifying a DNA clone that hybridizes with the isolated nucleic acid molecule of (a); and
(c) sequencing the genomic fragment that comprises the clone identified in step (b), wherein the sequenced genomic fragment encodes a carotenoid biosynthetic enzyme.

Similarly the invention provides a method for the identification of a gene encoding a lycopene β-cyclase which catalyzes the production of asymmetric carotenoids from acyclic carotenoids having at least one ψ-end group comprising:
(a) synthesizing an at least one oligonucleotide primer corresponding to a portion of a sequence selected from the group consisting of:
  (i) an isolated nucleic acid molecule encoding the amino acid sequence selected from the group consisting of SEQ ID NO:2 and SEQ ID NO:4;
  (ii) an isolated nucleic acid molecule that hybridizes with (i) under the following hybridization conditions: 0.1×SSC, 0.1% SDS, 65° C. and washed with 2×SSC, 0.1% SDS followed by 0.1×SSC, 0.1% SDS; and (iii) an isolated nucleic acid molecule that encodes a polypeptide having at least 70% identity to the polypeptides selected from the group consisting of SEQ ID NO:2 and SEQ ID NO:4 based on the Smith-Waterman method of alignment; and (b) amplifying an insert present in a cloning vector using the oligonucleotide primer of step (a);

wherein the amplified insert encodes a portion of an amino acid sequence encoding a carotenoid biosynthetic enzyme.

BRIEF DESCRIPTION OF THE DRAWINGS AND SEQUENCE DESCRIPTIONS

Figure 1:
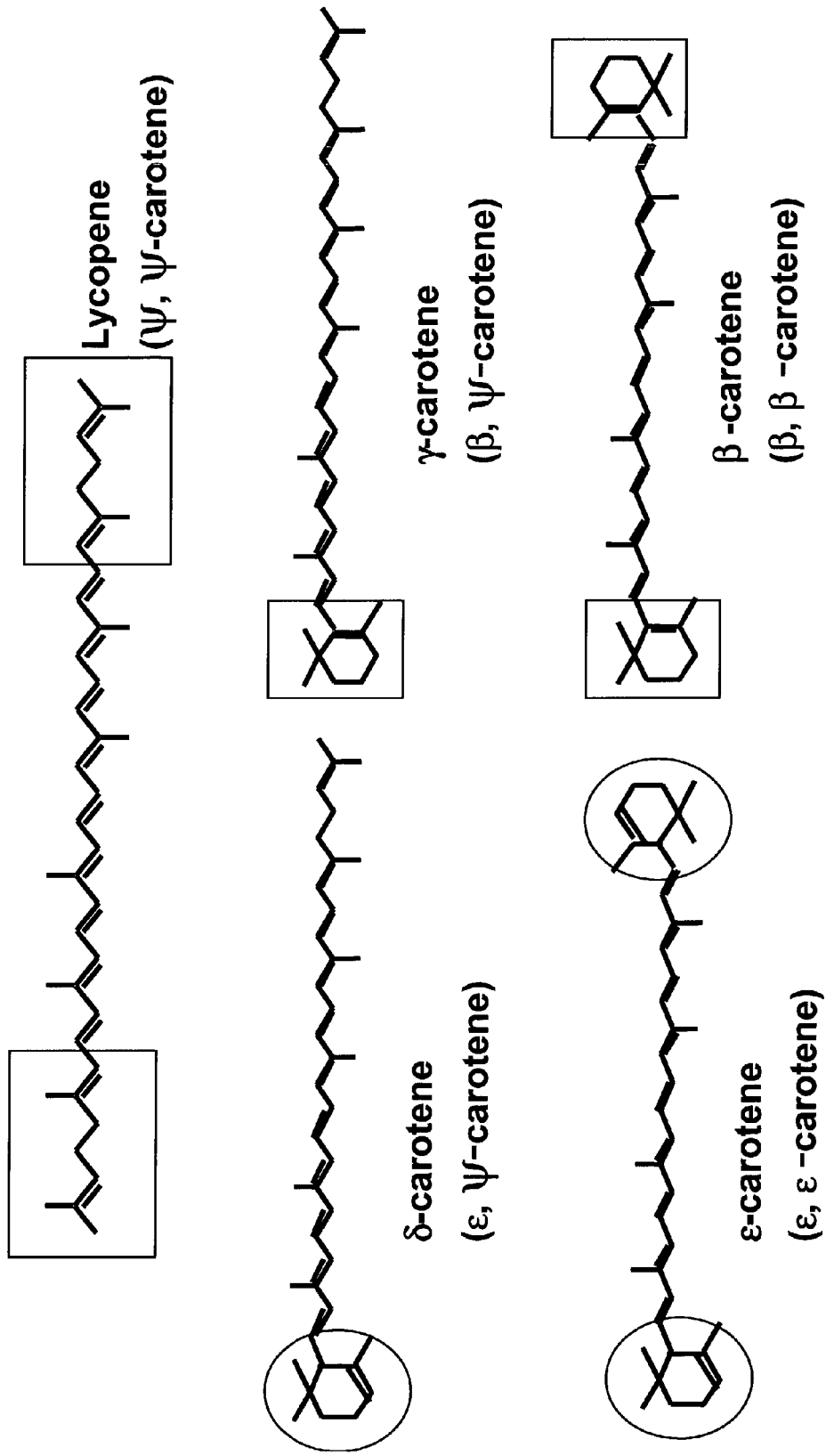
FIG. 1 illustrates the carotenoid structures of the acyclic end group (ψ group) or the cyclic end groups (β-ionone ring or ε-ionone ring).

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1 is the nucleotide sequence encoding the crtL gene from *Rhodococcus erythropolis* strain AN12.

SEQ ID NO:2 is the deduced amino acid sequence of crtL gene from *Rhodococcus erythropolis* strain AN12.

SEQ ID NO:3 is the nucleotide sequence encoding the CrtL gene from *Deinococcus radiodurans* strain R1 (ATCC 13939).

SEQ ID NO:4 is the deduced amino acid sequence of crtL gene from *Deinococcus radiodurans* strain R1 (ATCC 13939).

SEQ ID NOs:5–6 are the primer sequences used for amplifying the crtEXYIB gene cluster from *Pantoea stewartii* (ATCC 8199).

SEQ ID NOs:7–9 are the primer sequences used during amplification and/or sequencing of the 16s rRNA from *Rhodococcus erythropolis* strain AN12.

SEQ ID NO:10 is the first of two of the primers used for PCR amplification of *Rhodococcus erythropolis* strain AN12 lycopene cyclase crtL gene designated as AN12wtY-F.

SEQ ID NO:11 is the second of two primers used for PCR amplification of *Rhodococcus erythropolis* strain AN12 lycopene cyclase crtL gene designated as AN12wtY-R.

SEQ ID NO:12 is the first of two of the primers used for PCR amplification of *Deinococcus radiodurans* strain R1 (ATCC 13939) lycopene cyclase crtL gene designated as crtY_F(Deino).

SEQ ID NO:13 is the second of two of the primers used for PCR amplification of *Deinococcus radiodurans* strain R1 (ATCC 13939) lycopene cyclase crtL gene designated as crtY_R(Deino).

SEQ ID NO:14 is the first of two of the primers used for PCR amplification of *Pantoea stewartii* (ATCC 8199) lycopene cyclase CrtY gene designated as crtY_F.

SEQ ID NO:15 is the second of two of the primers used for PCR amplification of *Pantoea stewartii* (ATCC 8199) lycopene cyclase crtY gene designated as crtY_R.

DETAILED DESCRIPTION OF THE INVENTION

The present invention provides a biological method for producing asymmetric monocyclic carotenoids containing a single β-ionone ring end group. The method employs a host cell capable of producing acyclic carotenoids with at least one ψ-end group where the host cell expresses a specific lycopene β-cyclase capable of converting acyclic carotenoids to the corresponding asymmetric carotenoid.

The genes, associated gene products, and methods described herein enable one to selectively produce asymmetric, cyclic carotenoids having a single β-ionone ring. Potential areas of commercial application include, but are not limited to, pharmaceuticals, food supplements, animal feed additives, pigments, and eletro-optic applications such as photovoltaic devices. The unique lycopene β-cyclase (CrtL from *Rhodococcus erythropolis* AN12 or *Deinococcus radiodurans* strain R1 (ATCC 13939)) catalyzes the formation of the monocyclic (β-ionone ring) carotenoid γ-carotene, a more desirable product for some of the above-mentioned applications.

In this disclosure, a number of terms and abbreviations are used.

The following definitions are provided.

"Open reading frame" is abbreviated ORF.

"Polymerase chain reaction" is abbreviated PCR.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "isoprenoid" or "terpenoid" refers to the compounds and any molecules derived from the isoprenoid pathway including 10 carbon terpenoids and their derivatives, such as carotenoids and xanthophylls.

The terms "ψ end group" is defined as the $C_9H_{15}$ shown as the boxed acyclic structure in lycopene (FIG. 1).

The terms "β-ionone ring" or "β-ionone group" is defined as the $C_9H_{15}$ shown as the boxed cyclic structure in γ-carotene or β-carotene (FIG. 1).

The terms "ε-ionone ring" or "ε-ionone group" is defined as the $C_9H_{15}$ shown as the circled cyclic structure in δ-carotene or ε-carotene (FIG. 1).

The term "*Pantoea stewartii* subsp. *stewartii*" is abbreviated as "*Pantoea stewartii*" and is used interchangeably with *Erwinia stewartii* (Mergaert et al., *Int J. Syst. Bacteriol.* 43:162–173 (1993)).

The term "*Pantoea ananatas*" is used interchangeably with *Erwinia uredovora* (Mergaert et al., *Int J Syst. Bacteriol* 43:162–173 (1993)).

The terms "lycopene β-cyclase" or "β-cyclase" will be used interchangeably and refer to an enzyme that catalyzes the formation of a β-ionone ring cyclic end group from the acyclic ψ-end group.

The terms "lycopene ε-cyclase" or "ε-cyclase" will be used interchangeably and refer to an enzyme that catalyzes the formation of an ε-ionone ring cyclic end group from the acyclic ψ-end group.

The terms "*Rhodococcus erythropolis* AN12" or "AN12" will be used interchangeably and refer to the *Rhodococcus erythropolis* AN12 strain.

The term "*Deinococcus radiodurans* strain R1 (ATCC 13939)" or "*Deinococcus* R1" or "ATCC 13939" will be used interchangeably and refers to *Deinococcus radiodurans* R1 (ATCC 13939) strain.

The term "*Pantoea* crtEXYIB cluster" refers to a gene cluster containing carotenoid synthesis genes crtEXYIB amplified from *Pantoea stewartii* ATCC 8199. The gene cluster contains the genes crtE, crtX, crtY, crtI, and crtB. The cluster also contains a crtZ gene organized in opposite direction adjacent to crtB gene.

The term "CrtE" refers to geranylgeranyl pyrophosphate synthase enzyme encoded by crtE gene which converts trans-trans-farnesyl diphosphate+isopentenyl diphosphate to pyrophosphate+geranylgeranyl diphosphate.

The term "CrtY" refers to lycopene cyclase enzyme encoded by crY gene that converts lycopene to beta-carotene.

The term "CrtI" refers to phytoene dehydrogenase enzyme encoded by crtI gene that converts phytoene into lycopene via the intermediaries of phytofluene, zeta-carotene and neurosporene by the introduction of 4 double bonds The term "CrtB" refers to phytoene synthase enzyme encoded by crtB gene that catalyzes reaction from prephytoene diphosphate (geraylgeranyl pyrophosphate) to phytoene.

The term "CrtX" refers to zeaxanthin glucosyl transferase enzyme encoded by crtX gene that converts zeaxanthin to zeaxanthin-β-diglucoside.

The term "CrtZ" refers to the β-carotene hydroxylase enzyme encoded by crtZ gene which catalyses hydroxylation reaction from beta-carotene to zeaxanthin.

The term "carotenoid biosynthetic enzyme" is an inclusive term referring to any and all of the enzymes encoded by the *Pantoea* crtEXYIB cluster. The enzymes include CrtE, CrtY, CrtI, CrtB, and CrtX.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. For example a common set of stringent conditions consists of hybridization at 0.1×SSC, 0.1% SDS, 65° C. and washed with 2×SSC, 0.1% SDS followed by 0.1×SSC, 0.1% SDS.

One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Hybridization requires that the two nucleic acids contain complementary sequences although, depending on the stringency of the hybridization, mismatches between bases are possible. The appropriate stringency for hybridizing nucleic acids depends on the length of the nucleic acids and the degree of complementation, variables well known in the art. The relative stability (corresponding to higher Tm) of nucleic acid hybridization decreases in the following order: RNA:RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

A "substantial portion" or "portion" of an amino acid or nucleotide sequence comprising enough of the amino acid sequence of a polypeptide or the nucleotide sequence of a gene to putatively identify that polypeptide or gene, either by manual evaluation of the sequence by one skilled in the art, or by computer-automated sequence comparison and identification using algorithms such as BLAST (Basic Local Alignment Search Tool; Altschul et al., *J. Mol. Biol.* 215: 403–410 (1993); see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to specifically identify and/or isolate a nucleic acid fragment comprising the sequence. The instant specification teaches partial or complete amino acid and nucleotide sequences encoding one or more particular microbial proteins. The skilled artisan, having the benefit of the sequences as reported herein, may now use all or a substantial portion of the disclosed sequences for purposes known to those skilled in this art.

The term "complementary" is used to describe the relationship between nucleotide bases that are capable to hybridizing to one another. For example, with respect to DNA, adenosine is complementary to thymine and cytosine is complementary to guanine.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, NY (1988); *Biocomputing: Informatics and Genome Projects* (Smith, D. W., ed.) Academic Press, NY (1993); *Computer Analysis of Sequence Data, Part I* (Griffin, A. M., and Griffin, H. G., eds.) Humana Press, NJ (1994); *Sequence Analysis in Molecular Biology* (von Heinje, G., ed.) Academic Press (1987); and *Sequence Analysis Primer* (Gribskov, M. and Devereux, J., eds.) Stockton Press, NY (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignments of the sequences were performed using the Clustal method of alignment (Higgins et al., *CABIOS.* 5:151–153 (1989)) with the default parameters (GAP PENALTY=10, GAP LENGTH PENALTY=10). Default parameters for pair-wise alignments using the Clustal method were KTUPLE 1, GAP PENALTY=3, WINDOW=5 and DIAGONALS SAVED=5.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID Nos. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters, which cause a gene to be expressed in most cell types at most times, are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "altered biological activity" will refer to an activity, associated with a protein encoded by a microbial nucleotide sequence which can be measured by an assay method, where that activity is either greater than or less than the activity associated with the native microbial sequence. "Enhanced biological activity" refers to an altered activity that is greater than that associated with the native sequence. "Diminished biological activity" is an altered activity that is less than that associated with the native sequence.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides a method for producing asymmetric monocyclic carotenoids using a CrtL enzyme from *Rhodococcus* and *Deinococcus* that selectively catalyzes the formation of monocyclic carotenoids (β-ionone ring end group) from ψ end groups found on acyclic carotenoids.

The invention provides an isolated lycopene β-cyclase (CrtL) from *Rhodococcus* (SEQ ID NOs:1–2) and *Deinococcus* (SEQ ID NOs:3–4) which specifically produces only monocyclic (β-ionone ring) carotenoids (i.e. γ-carotene) from the acyclic carotenoid, lycopene. Additionally the invention provides a method for producing monocyclic carotenoids using the novel functionality of the present encoded enzymes.

The lycopene β-cyclase polypeptide isolated from *Rhodococcus* shared homology (31% identity, 45% similarity, E-value=2e-37) to a putative carotenoid lycopene β-cyclase DR0801 (GenBank® ID AAF10377.1) from *Deinococcus radiodurans* and other CrtL-type of lycopene β-cyclases from plants as shown by BLAST analysis. Unlike the CrtL from *Rhodococcus* and *Deinococcus*, the CrtL-type lycopene β-cyclases from photosynthetic bacteria (Cunningham et al., *Plant Cell*. 6: 1107–1121 (1994)) and plants (Hugueney et al., *Plant J*. 8: 417–424 (1995)) have been shown to catalyze a double cyclization or carotenoid substrates and to convert lycopene to bicyclic β-carotene.

Comparison of the CrtL-type lycopene β-cyclases isolated from *Rhodococcus* or *Deinococcus* to nucleotide base and deduced amino acid sequences to public databases reveals that the most similar known sequences is about 31% identical to the amino acid sequence of reported herein over length of 410 amino acid using a Smith-Waterman alignment algorithm (W. R. Pearson, Comput. Methods Genome Res., [Proc. Int. Symp.] (1994), Meeting Date 1992, 111–20. Editor(s): Suhai, Sandor. Publisher: Plenum, New York, N.Y.). Preferred amino acid fragments are at least about 70%–80% identical herein. More preferred are nucleic acid fragments that are at least 80%–90% identical to the sequences herein. Most preferred are nucleic acid fragments that are at least 95% identical to the amino acid fragments reported herein. Similarly, preferred *Rhodococcus* or *Deino-*

*coccus* CrtL-type lycopene β-cyclases encoding nucleic acid sequences corresponding to the instant ORF's are those encoding active proteins and which are at least 80% identical to the nucleic acid sequences of reported herein. More preferred CrtL-type lycopene β-cyclase nucleic acid fragments are at least 90% identical to the sequences herein. Most preferred are CrtL-type lycopene β-cyclase nucleic acid fragments that are at least 95% identical to the nucleic acid fragments reported herein.

Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

Isolation of Homologs

This method of instant invention may be used to produce monocyclic carotenoids containing a single β-ionone ring end group (i.e. γ-carotene and its derivatives) using a lycopene β-cyclase enzyme (CrtL) isolated from *Rhodococcus* and *Deinococcus* which has the unique property of selectively catalyzing the formation of monocyclic carotenoids. The CrtL enzyme used in the method of instant invention may be used to isolate genes encoding homologous proteins from the same or other microbial species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g. polymerase chain reaction (PCR), Mullis et al., U.S. Pat. No. 4,683,202), ligase chain reaction (LCR), Tabor et al., *PNAS* 82: 1074, (1985)) or strand displacement amplification (SDA; Walker et al., *PNAS* 89: 392 (1992)).

For example, genes encoding similar proteins or polypeptides to those of the enzymes used in the instant invention could be isolated directly by using all or a portion of the instant nucleic acid fragments as DNA hybridization probes to screen libraries from any desired bacteria using methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full-length DNA fragments under conditions of appropriate stringency.

Typically, in PCR-type amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Virginia; Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally two short segments of the instant sequences may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes.

Alternatively, the second primer sequence may be based upon sequences derived from the cloning vector. For example, the skilled artisan can follow the RACE protocol (Frohman et al., *PNAS* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (GibcoBRL—Life Technologies, Rockville, Md.), specific 3' or 5' cDNA fragments can be isolated (Ohara et al., *PNAS USA* 86:5673 (1989); Loh et al., *Science* 243:217 (1989)).

Alternatively the disclosed sequences may be employed as hybridization reagents for the identification of homologs. The basic components of a nucleic acid hybridization test include a probe, a sample suspected of containing the gene or gene fragment of interest, and a specific hybridization method. Probes used for identification of the crtL gene that encodes the CrtL lycopene β-cyclase used in the present invention are typically single stranded nucleic acid sequences that are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally, a chaotropic agent may be added. The chaotropic agent stabilizes nucleic acids by inhibiting nuclease activity. Furthermore, the chaotropic agent allows sensitive and stringent hybridization of short oligonucleotide probes at room temperature (Van Ness and Chen, *Nucl. Acids Res.* 19:5143–5151 (1991)). Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1M sodium chloride, about 0.05 to 0.1M buffers, such as sodium citrate, Tris-HCI, PIPES or HEPES (pH range about 6–9), about 0.05 to 0.2% detergent, such as sodium dodecylsulfate, or between 0.5–20 mM EDTA, FICOLL (Pharmacia Biotech, Milwaukee, Wis.) (about 300–500 kilodaltons), polyvinylpyrrolidone (about 250–500 kD), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt./vol. glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Nucleic acid hybridization is adaptable to a variety of assay formats. One of the most suitable is the sandwich assay format. The sandwich assay is particularly adaptable to hybridization under non-denaturing conditions. A primary component of a sandwich-type assay is a solid support. The solid support has adsorbed to it or covalently coupled to it immobilized nucleic acid probe that is unlabeled and complementary to one portion of the sequence.

Microbial Production of Asymmetric Carotenoids

Asymmetric carotenoids of the present invention may be produced using microbial host cells. The host cells will preferably express a lycopene β-cyclase having the ability to convert acyclic carotenoids substrates to the corresponding asymmetric carotenoid. In one embodiment the)host cells may have the ability to produce acyclic carotenoids endogenously. In another embodiment the acyclic carotenoid substrate may be added to the host cell exogenously.

Preferred heterologous host cells for expression of the disclosed genes and nucleic acid fragments can comprise microbial hosts that can be found broadly within the fungal or bacterial families and which grow over a wide range of temperature, pH values, and solvent tolerances. For example, it is contemplated that any of bacteria, yeast, and filamentous fungi will be suitable hosts for expression of the present nucleic acid fragments. Because of transcription, translation and the protein biosynthetic apparatus is the same irrespective of the cellular feedstock, functional genes are expressed irrespective of carbon feedstock used to generate cellular biomass. Large-scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of host strains include but are not limited to bacterial, fungal or yeast species such as *Aspergillus, Trichoderma, Saccharomyces, Pichia, Candida, Hansenula,* or bacterial species such as *Salmonella, Bacillus, Acinetobacter, Zymomonas, Agrobacterium, Erythrobacter, Chlorobium, Chromatium, Flavobacterium, Cytophaga, Rhodobacter, Rhodococcus, Streptomyces, Brevibacterium, Corynebacteria, Mycobacterium, Deinococcus, Escherichia, Erwinia, Pantoea, Pseudomonas, Sphingomonas, Methylomonas, Methylobacter, Methylococcus, Methylosinus, Methylomicrobium, Methylocystis, Alcaligenes, Synechocystis, Synechococcus, Anabaena, Thiobacillus, Methanobacterium, Klebsiella,* and *Myxococcus*.

Microbial expression systems and expression vectors containing regulatory sequences that direct high level expression of foreign proteins are well known to those skilled in the art. Any of these could be used to construct chimeric genes for expression of present β-cyclases. These chimeric genes could then be introduced into appropriate microorganisms via transformation to provide high-level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$. $IP_R$. T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

Accordingly it is expected, for example, that introduction of chimeric gene encoding the instant bacterial enzymes under the control of the appropriate promoters, will demonstrate increased or altered cyclic carotenoid production. It is contemplated that it will be useful to express the instant genes both in natural host cells as well as heterologous host. Introduction of the present crtL genes into native host will result in altered levels of existing carotenoid production. Additionally, the instant genes may also be introduced into non-native host bacteria where the existing carotenoid pathway may be manipulated.

Specific monocyclic carotenoids that may be produced by the present invention include, but are not limited to, γ-carotene, β-zeacarotene, 3-hydroxy-β-zeacarotene, 4-keto-γ-carotene, torulene, 3-hydroxy-3',4'-didehydro-β,ψ-carotene-4-one (HDCO), 3,3'-dihydroxy-β-ψ-carotene-4,4'-dione (DCD), chlorobactene, rubixanthin (3-hydroxy-γ-carotene), 4-keto-rubixanthin, 4-keto-torulene, flexixanthin (1',2'-dihydro-1'-hydroxy-3-hydroxy-4-keto-torulene), myxobactone, α-carotene, and lutein. The specific preferred substrate for the present CrtL enzyme is the ψ-end group on acyclic carotenoids, such as lycopene or neurosporene. Accordingly, preferred acyclic carotenoid substrates include but are not limited to lycopene, neurosporene, didehydrolycopene, lycoxanthin (16-hydroxylycopene), 1-hydroxy-1,2-dihydroneurosporene, 1-hydroxy-1,2-dihydrolycopene, 1,2-dihydro-3,4-dehydro-1-hydroxylycopene, and δ-carotene.

Many suitable host cells will contain various elements of the carotenoid biosynthetic pathway and will have the ability to endogenously produce the appropriate acyclic carotenoid substrates. Where the necessary genetic machinery is absent for production of the substrate, a host cell may optionally be engineered to contain the necessary genes for the production of the substrate. Generally only three genes will be needed. At least one copy of a gene encoding a geranylgeranyl pyrophosphate synthase enzyme; at least one copy of a gene encoding a phytoene synthase enzyme; and at least one copy of a gene encoding a phytoene dehydrogenase enzyme. These elements of the carotenoid biosynthetic pathway have been isolated from a variety of organisms and their sequences are available in the art. For example, these genes are indexed in public databases as indicated in the chart below:

| Gene | GenBank ® Accession Number and Source Organism |
|---|---|
| CrtE (GGPP Synthase) | AB000835, *Arabidopsis thaliana* |
| | AB016043 and AB019036, *Homo sapiens* |
| | AB016044, *Mus musculus* |
| | AB027705 and AB027706, *Daucus carota* |
| | AB034249, *Croton sublyratus* |
| | AB034250, *Scoparia dulcis* |
| | AF020041, *Helianthus annuus* |
| | AF049658, *Drosophila melanogaster* signal recognition particle 19kDa protein (srp19) gene, partial sequence; and geranylgeranyl pyrophosphate synthase (quemao) gene, complete cds |
| | AF049659, *Drosophila melanogaster* geranylgeranyl pyrophosphate synthase mRNA, complete cds |
| | AF139916, *Brevibacterium linens* |
| | AF279807, *Penicillium paxilli* geranylgeranyl pyrophosphate synthase (ggs1) gene, complete |
| | AF279808 *Penicillium paxilli* dimethylallyl tryptophan synthase (paxD) gene, partial cds; and cytochrome P450 monooxygenase (paxQ), cytochrome P450 monooxygenase (paxP), PaxC (paxC), monooxygenase (paxM), geranylgeranyl pyrophosphate synthase (paxG), PaxU (paxU), and metabolite transporter (paxT) genes, complete cds |
| | AJ010302, *Rhodobacter sphaeroides* |
| | AJ133724, *Mycobacterium aurum* |
| | AJ276129, *Mucor circinelloides* f. lusitanicus carG gene for geranylgeranyl pyrophosphate synthase, exons 1–6 |
| | D85029 *Arabidopsis thaliana* mRNA for geranylgeranyl pyrophosphate synthase, partial cds |
| | L25813, *Arabidopsis thaliana* |
| | L37405, *Streptomyces griseus* geranylgeranyl pyrophosphate synthase (crtB), phytoene desaturase (cftE) and phytoene synthase (cftI) genes, complete cds |
| | U15778, *Lupinus albus* geranylgeranyl pyrophosphate synthase (ggps1) mRNA, complete cds |
| | U44876, *Arabidopsis thaliana* pregeranylgeranyl pyrophosphate synthase (GGPS2) mRNA, complete cds |
| | X92893, *C. roseus* |
| | X95596, *S. griseus* |
| | X98795, *S. alba* |
| | Y15112, *Paracoccus marcusii* |
| crtB | AB001284, *Spirulina platensis* |
| | AB032797, *Daucus carota* PSY mRNA for phytoene synthase, complete cds |
| | AB034704, *Rubrivivax gelatinosus* |
| | AB037975, *Citrus unshiu* |
| | AF009954, *Arabidopsis thaliana* phytoene synthase (PSY) gene, complete cds |
| | AF139916, Brevibacterium linens |
| | AF152892, *Citrus x paradisi* |
| | AF218415, *Bradyrhizobium sp.* ORS278 |
| | AF220218, *Citrus unshiu* phytoene synthase (Psy1) mRNA, complete cds |
| | AJ010302, Rhodobacter |
| | AJ133724, *Mycobacterium aurum* |
| | AJ278287, *Phycomyces blakesleeanus* carRA gene for lycopene cyclase/phytoene synthase, |
| | AJ304825 *Helianthus annuus* mRNA for phytoene synthase (psy gene) |
| | AJ308385 *Helianthus annuus* mRNA for phytoene synthase (psy gene) |
| | D58420, *Agrobacterium aurantiacum* |
| | L23424 *Lycopersicon esculentum* phytoene synthase (PSY2) mRNA, complete cds |
| | L25812, Arabidopsis |
| | L37405, *Streptomyces griseus* geranylgeranyl pyrophosphate synthase (crtB), phytoene desaturase (cftE) and phytoene synthase (cftl) genes, complete cds |
| | M38424 *Pantoea agglomerans* phytoene synthase (crtE) gene, complete cds |
| | M87280, *Pantoea agglomerans* |
| | S71770, carotenoid gene cluster |
| | U32636 Zea mays phytoene synthase (Y1) gene, complete cds |
| | U62808, Flavobacterium ATCC21588 |
| | U87626, *Rubrivivax gelatinosus* |
| | U91900, *Dunaliella bardawil* |
| | X52291, *Rhodobacter capsulatus* |
| | X60441, *L. esculentum* GTom5 gene for phytoene synthase |
| | X63873 Synechococcus PCC7942 pys gene for phytoene synthase |
| | X68017 *C. annuum* psy1 mRNA for phytoene synthase |
| | X69172 Synechocystis sp. pys gene for phytoene synthase |
| | X78814, *N. pseudonarcissus* |
| crtI | AB046992, *Citrus unshiu* CitPDS1 mRNA for phytoene desaturase, complete cds |
| | AF039585 *Zea mays* phytoene desaturase (pds1) gene promoter region and exon 1 |
| | AF049356 *Oryza sativa* phytoene desaturase precursor (Pds) mRNA, complete cds |
| | AF139916, *Brevibacterium linens* |
| | AF218415, *Bradyrhizobium sp.* ORS278 |
| | AF251014, *Tagetes erecta* |
| | AF364515, *Citrus x paradisi* |
| | D58420, *Agrobacterium aurantiacum* |
| | D83514, *Erythrobacter longus* |
| | L16237, *Arabidopsis thaliana* |
| | L37405, *Streptomyces griseus* geranylgeranyl pyrophosphate synthase (crtB), phytoene desaturase (cftE) and phytoene synthase (cftI) genes, complete cds |

-continued

| Gene | GenBank ® Accession Number and Source Organism |
|---|---|
| | L39266, *Zea mays* phytoene desaturase (Pds) mRNA, complete cds |
| | M64704, Soybean phytoene desaturase |
| | M88683, *Lycopersicon esculentum* phytoene desaturase (pds) mRNA, complete cds |
| | S71770, carotenoid gene cluster |
| | U37285, *Zea mays* |
| | U46919, *Solanum lycopersicum* phytoene desaturase (Pds) gene, partial cds |
| | U62808, Flavobacterium ATCC21588 |
| | X55289, Synechococcus pds gene for phytoene desaturase |
| | X59948, *L. esculentum* |
| | X62574, *Synechocystis sp.* pds gene for phytoene desaturase |
| | X68058 *C. annuum* pds1 mRNA for phytoene desaturase |
| | X71023 *Lycopersicon esculentum* pds gene for phytoene desaturase |
| | X78271, *L. esculentum* (Ailsa Craig) PDS gene |
| | X78434, *P. blakesleeanus* (NRRL1555) carB gene |
| | X78815, *N. pseudonarcissus* |
| | X86783, *H. pluvialis* |
| | Y14807, *Dunaliella bardawil* |
| | Y15007, *Xanthophyllomyces dendrorhous* |
| | Y15112, *Paracoccus marcusii* |
| | Y15114, Anabaena PCC7210 crtP gene |
| | Z11165, *R. capsulatus* |

Alternatively, where the substrate is not synthesized endogenously by the host cell it will be possible to add the substrate exogenously. In this embodiment the suitable carotenoid substrate may be solubilized with mild detergent (eg, DMSO) or mix with phospholipid vesicles. To assist in transport into the cell the host cell may optionally be permeabilized with a suitable solvent such as toluene. Methods for this type of in vitro bio-conversion of carotenoid substrates has basis in the art, see for example Hundle et al., *FEBS*, 315:329–334 (1993) and Bramley et al., *Phytochemistry*, 26:1935–1939 (1987)).

Pathway Modulation

Knowledge of the sequence of the present enzyme used in the method will be useful in manipulating the carotenoid biosynthetic pathways in any organism having such a pathway and particularly in methanotrophs. Methods of manipulating genetic pathways are common and well known in the art. Selected genes in a particularly pathway may be upregulated or down regulated by variety of methods. Additionally, competing pathways organism may be eliminated or sublimated by gene disruption and similar techniques.

Once a key genetic pathway has been identified and sequenced specific genes may be upregulated to increase the output of the pathway. For example, additional copies of the targeted genes may be introduced into the host cell on multicopy plasmids such as pBR322. Alternatively the target genes may be modified so as to be under the control of non-native promoters. Where it is desired that a pathway operate at a particular point in a cell cycle or during a fermentation run, regulated or inducible promoters may used to replace the native promoter of the target gene. Similarly, in some cases the native or endogenous promoter may be modified to increase gene expression. For example, endogenous promoters can be altered in vivo by mutation, deletion, and/or substitution (see, Kmiec, U.S. Pat. No. 5,565,350; Zarling et al., PCT/US93/03868).

Alternatively it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods of gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al., *J. Bacteriol.* 171:4617–4622 (1989); Balbas et al., *Gene* 136:211–213 (1993); Gueldener et al., *Nucleic Acids Res.* 24:2519–2524 (1996); and Smith et al., *Methods Mol. Cell. Biol.* 5:270–277 (1996))

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA that encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frameshift mutations. Specific methods for creating mutants using radiation or chemical agents are well documented in the art (see for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36:227 (1992)).

Another non-specific method of gene disruption is the use of transposable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutageneis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element).

Industrial Production

Where commercial production of β-ionone ring based monocyclic, and hence, asymmetric carotenoids are desired using the present crtL genes, a variety of culture methodologies may be applied. For example, large-scale production of a specific gene product over-expressed from a recombinant microbial host may be produced by either batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of monocyclic carotenoids may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. Suitable substrates may include but are not limited to monosaccharides such as glucose and fructose, oligosaccharides such as lactose or sucrose, polysaccharides such as starch or cellulose or mixtures thereof and unpurified mixtures from renewable feedstocks such as cheese whey permeate, cornsteep liquor, sugar beet molasses, and barley malt. Additionally the carbon substrate may also be one-carbon substrates such as carbon dioxide, methane or methanol for which metabolic conversion into key biochemical intermediates has been demonstrated. In addition to one and two carbon substrates methylotrophic organisms are also known to utilize a number of other carbon containing compounds such as methylamine, glucosamine and a variety of amino acids for metabolic activity. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Recombinant Expression—Plants

Plants and algae are also known to produce carotenoids. The nucleic acid fragments of the instant invention may be used to create transgenic plants having the ability to express the microbial protein. Preferred plant hosts will be any variety that will support a high production level of the instant proteins. Suitable green plants will include but are not limited to soybean, rapeseed (*Brassica napus, B. campestris*), pepper, sunflower (*Helianthus annus*), cotton (*Gossypium hirsutum*), corn, tobacco (*Nicotiana tabacum*), alfalfa (*Medicago saliva*), wheat (*Triticum* sp), barley (*Hordeum vulgare*), oats (*Avena sativa*, L), sorghum (*Sorghum bicolor*), rice (*Oryza saliva*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include, but not limited to, commercially significant hosts such as *Spirulina, Haemotacoccus,* and *Dunalliela*. Production of the carotenoid compounds may be accomplished by first constructing chimeric genes of present invention in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high-level plant promoter. Such promoters, in operable linkage with the genetic sequences or the present invention should be capable of promoting expression of the present gene product. High-level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (see, for example, *Genetic Engineering of Plants, an Agricultural Perspective*, A. Cashmore, Plenum, N.Y. (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA blots (Southern, *J. Mol. Biol.* 98: 503, (1975)). Northern analysis of mRNA expression (Kroczek, J. *Chromatogr. Biomed. Appl.*, 618 (1–2) 133–145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J., *Ann. Rev., Plant Phys. Plant Mol. Biol.* 42:21–53 (1991)), or nuclear localization signals (Raikhel, N., *Plant Phys.* 100: 1627–1632 (1992)) added and/or with targeting sequences that are already present removed. While the references cited give examples of each of these, the list is not exhaustive and more targeting signals of utility may be discovered in the future that are useful in the invention.

DESCRIPTION OF THE PREFERRED EMBODIMENTS

Applicants have isolated a lycopene β-cyclase (CrtL) from *Rhodococcus* (SEQ ID NOs:1–2) and *Deinococcus* (SEQ ID NOs:3–4) which specifically produces only monocyclic (β-ionone ring) carotenoids (i.e. γ-carotene) from the acyclic carotenoid, lycopene. These genes are used in methods for the production of the corresponding monocyclic carotenoids.

An environmental sample containing a *Rhodococcus erythropolis* AN12 strain was obtained from a wastewater treatment facility. One ml of activated sludge was inoculated directly into 10 ml of S12 medium. Aniline was used as the sole source of carbon and energy. The culture was maintained by addition of 100 ppm aniline every 2–3 days. The culture was diluted (1:100 dilution) every 14 days. Bacteria that utilize aniline as a sole source of carbon and energy were further isolated and purified on S12 agar. Aniline (5 μL) was placed on the interior of each culture dish lid (Example 1).

When the 16s rRNA gene of *Rhodococcus* AN12 was sequenced and compared to other 16s rRNA sequence in the GenBank® sequence database, the 16s rRNA gene of AN12 strain was found to be at least 98% similarity to the 16s rRNA gene sequences of high G+C gram-positive *Rhodococcus* genus (Example 1).

The *Rhodococcus erythropolis* strain AN12 is naturally pigmented. The carotenoid pigments from this strain were isolated and analyzed via an HPLC with a photodiode array detector (Example 3). The spectrum of the peaks observed matched that of γ-carotene and one of its derivatives, 4-keto-γ-carotene. Molecular weight analysis of the two main carotenoids measured matched that of γ-carotene and 4-keto-γ-carotene. Previously reported bacterial lycopene β-cyclases have been shown to catalyze the formation of bicyclic β-carotene and its derivatives from lycopene via a γ-carotene intermediate. The analytical data from the isolated carotenoids suggested that the CrtL lycopene β-cyclase from *Rhodococcus erythropolis* strain AN12 selectively produced only monocyclic γ-carotene-like carotenoids.

A lycopene accumulating strain of *E. coli* was constructed as a reporter strain for assaying lycopene cyclase activity (Example 4). Briefly, the lycopene accumulating *E. coli* strain was created by first cloning the gene cluster crtEXYIB from *Pantoea stewartii* in *E. coli*, and then inserting a transposon in the crtY gene of the cluster. The cluster contained many of the genes required for the synthesis of carotenoids, and β-carotene was normally produced in the transformed *E. coli* with the wild type cluster (no transposon insert in the crtY gene). It should be noted that the crtZ gene (β-carotene hydroxylase) was included in the gene cluster. However, since no promoter was present to express the crtZ gene (organized in opposite direction and adjacent to crtB gene) no zeaxanthin was produced, and thus, the zeaxanthin glucosyl transferase enzyme (encoded by the crtX gene located within the gene cluster) had no substrate for its reaction.

Figure 2:
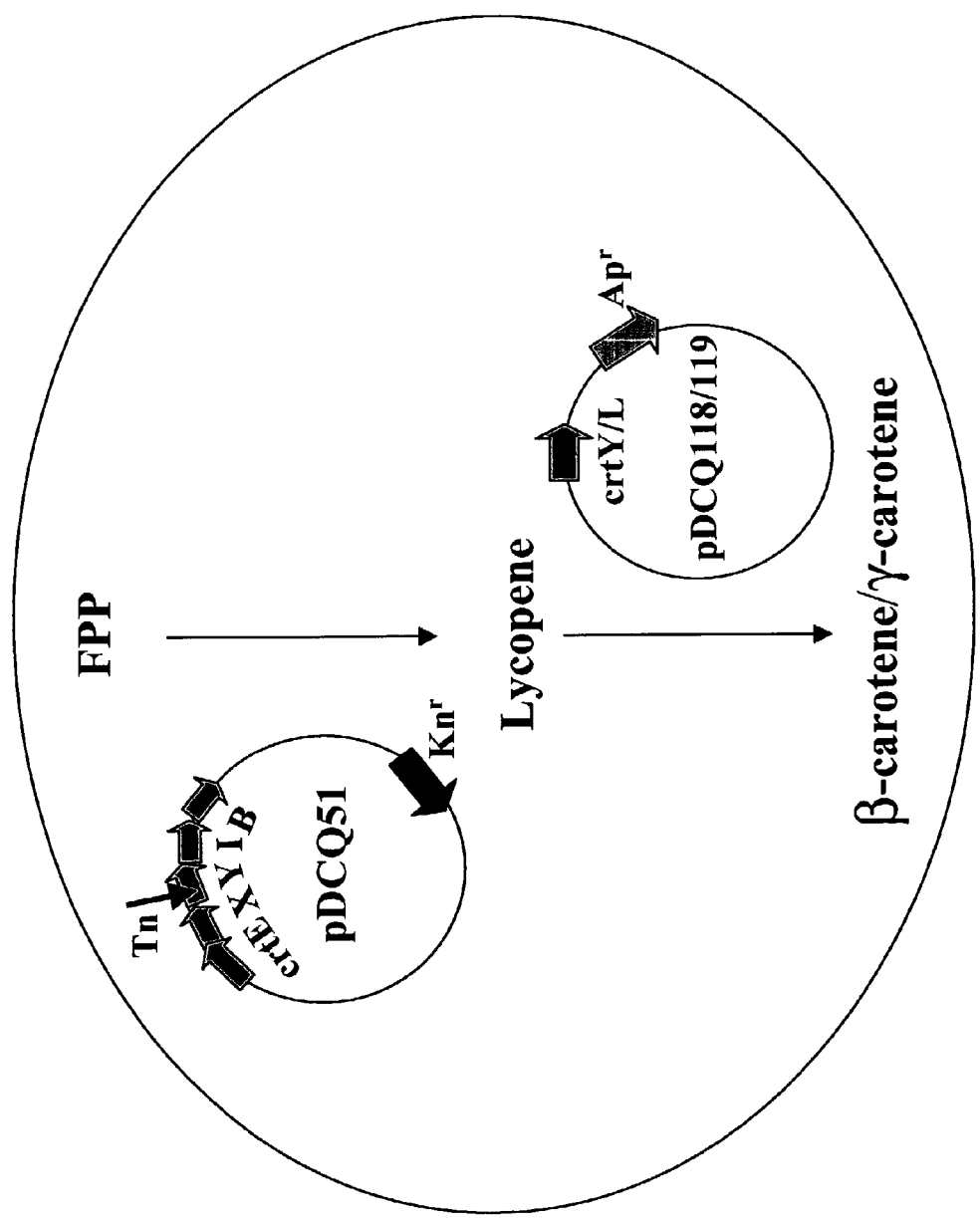
FIG. 2 illustrates the in vivo complementation of lycopene cyclase in the heterologous expression system MG1655(pDCQ51) with pDCQ118 or pDCQ119.

In vitro transposon mutagenesis was performed with the plasmid containing the wild type gene cluster. A series of plasmid constructs containing insertion mutations were generated and were transformed into the host *E. coli* strain MG1655. Various mutants were observed phenotypically based on the color of the colony produced. The carotenoids produced by the different strains were analyzed by HPLC. A pink mutant containing a transposon insertion in crtY gene accumulated lycopene. The crtY gene within the cluster encoded for a lycopene β-cyclase, an enzyme that catalyzes the formation of bicyclic carotenoids. The transposon insertion interrupted the synthesis of a functional CrtY enzyme, and thus, blocked synthesis of cyclic carotenoids, accumulating the acyclic precursor, lycopene (FIG. 2). The lycopene accumulating strain, designated as MG1655 (pDCQ51), was used as a reporter strain for assaying lycopene cyclase activity.

*Pantoea stewartii* has a classic bacterial CrtY-type of lycopene β-cyclase and is homologous to crtY of *Erwinia uredovora* which has been shown to convert lycopene to bicyclic β-carotene (Misawa et al., *J. Bacteriol.* 172:6704–6712 (1990)). The lycopene β-cyclase from *Rhodococcus* shared homology (31% identity, 45% similarity, E-value=2e-37) to a putative carotenoid lycopene β-cyclase DR0801 (GenBank® ID AAF10377.1) from *Deinococcus radiodurans* and other CrtL-type of lycopene β-cyclases from plants as shown by the BLAST analysis (Example 2). Unlike the CrtL from *Rhodococcus* and *Deinococcus*, the CrtL-type of lycopene β-cyclases isolated from photosynthetic bacteria (Cunningham et al., *Plant Cell*. 6: 1107–1121 (1994)) and plants (Hugueney et al., *Plant J*. 8: 417–424 (1995)) have been shown to catalyze a double cyclization of the carotenoid substrate in similar fashion to the CrtY enzymes for the conversion lycopene to bicyclic β-carotene.

In another embodiment, lycopene cyclase genes from *Pantoea stewartii* (ATCC 8199), *Rhodococcus erythropolis* AN12, and *Deinococcus radiodurans* R1 (ATCC 13939) were individually heterologously expressed in either a forward or reverse orientation in the *E. coli* reporter strain using a compatible expression vector (Example 5). The six plasmid constructs were confirmed by restriction analysis and sequencing. All transformants containing cyclase genes in reverse orientation were pink in color, indicating that the cells were still accumulating lycopene. The transformants expressing *Pantoea stewartii* lycopene β-cyclase enzyme CrtY (forward orientation) were yellow in color, indicating that the cells were no longer accumulating lycopene. The transformants containing the *Rhodococcus* and *Deinococcus* lycopene cyclase gene crtL (forward orientation) had an orange appearance, indicating that the cells were no longer accumulating lycopene and that the carotenoids produced were different from those containing the crtY gene.

The carotenoids produced by the six *E. coli* strains expressing different lycopene cyclases were analyzed by HPLC (Example 6). The lycopene accumulating strain (host only), all reverse orientation construct strains, and an authentic lycopene standard, all had peak retention times and identical absorption spectra indicating that the controls did not contain a functional lycopene cyclase enzyme (Table 1). The strain containing the *Pantoea* crtY gene in forward orientation contained a carotenoid which had a similar retention time and absorption spectra identical to a β-carotene standard. This data indicated that the crtY gene converted lycopene to the bicyclic β-carotene, typical of known bacterial β-cyclases. The strains containing either the *Rhodococcus* or *Deinococcus* crtL genes in forward orientation contained a carotenoid which had a retention time and absorption spectra indicative of γ-carotene, a monocyclic carotenoid containing a β-ionone ring. No β-carotene was produced in these two strains with crtL expression. The data suggests that the CrtL enzymes from the *Rhodococcus* or *Deinococcus* strains used, selectively produced only the monocyclic γ-carotene from lycopene as opposed to the β-carotene produced by *Pantoea* CrtY.

The CrtL enzymes that selectively catalyze the formation of monocyclic carotenoids can be used to create a variety of novel or rare asymmetric monocyclic carotenoids. Any acyclic carotenoid-like compound, in addition to lycopene, which contains a ψ end group can be expected to act as a substrate for the creation of novel or rare carotenoids.

The method described above could be used to produce such compounds in a variety of expression systems. The genes that encode for the CrtL enzymes having the unique functionality as described could be expressed in other expression systems, such as a plant expression system. The monocyclic carotenoids produced in such a system would thereby alter the nutritional, pharmacological, or appearance value of the organism.

Alternatively, an anti-sense strand of one of the citL genes described previously can be inserted into a suitable vector and subsequently incorporated into the genomic DNA of a host. The anti-sense strand would inhibit and control the profile of carotenoids produced in such organisms containing a functional crtL gene.

The unique functionality of the CrtL enzymes can be used to selectively make γ-carotene-like compounds from lycopene. The method and constructs described herein can be used to selectively produce monocyclic (hence asymmetric) γ-carotene-like carotenoids in a-variety of expression systems.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GibcoBRL—Life Technologies (Rockville, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were to used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "ml" means milliliters, "L" means liters.

Example 1

Isolation and Characterization of Strain AN12

Example 1 describes the isolation of strain AN12 of *Rhodococcus erythropolis* on the basis of being able to grow on aniline as the sole source of carbon and energy. Analysis of a 16S rRNA gene sequence indicated that strain AN12 was related to high G+C Gram positive bacteria belonging to the genus *Rhodococcus*.

Bacteria that grew on aniline were isolated from an enrichment culture. The enrichment culture was established by inoculating 1 ml of activated sludge into 10 ml of S12 medium (10 mM ammonium sulfate, 50 mM potassium phosphate buffer (pH 7.0), 2 mM $MgCl_2$, 0.7 mM $CaCl_2$, 50 µM $MnCl_2$, 1 µM $FeCl_3$, 1 µM $ZnCl_3$, 1.72 µM $CuSO_4$, 2.53 µM $CoCl_2$, 2.42 µM $Na_2MoO_2$, and 0.0001% $FeSO_4$) in a 125 ml screw cap Erlenmeyer flask. The activated sludge was obtained from a wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 ml of the culture with the same volume of S12 medium. Bacteria that utilized aniline as a sole source of carbon and energy were isolated by spreading samples of the enrichment culture onto S12 agar. Aniline (5 µL) was placed on the interior of each Petri dish lid. The Petri dishes were sealed with parafilm and incubated upside down at room temperature (approximately 25° C.). Representative bacterial colonies were then tested for the ability to use aniline as a sole source of carbon and energy. Colonies were transferred from the original S12 agar plates used for initial isolation to new S12 agar plates and supplied with aniline on the interior of each Petri dish lid. The Petri dishes were sealed with parafilm and incubated upside down at room temperature (approximately 25° C.).

The 16S rRNA genes of each isolate were amplified by PCR and analyzed as follows. Each isolate was grown on R2A agar (DIFCO Labs). Several colonies from a culture plate were suspended in 100 µl of water. The mixture was frozen and then thawed once. The 16S rRNA gene sequences were amplified by PCR using a commercial kit according to the manufacturer's instructions (Perkin Elmer, Boston, Mass.) with primers HK12 (5'-GAGTTTGATCCTGGCT-CAG-3') (SEQ ID NO:7) and HK13 (5'-TACCTTGTTAC-GACTT-3') (SEQ ID NO:8). PCR was performed in a Perkin Elmer GeneAmp® 9600 (Norwalk, Conn.). The samples were incubated for 5 min at 94° C. and then cycled 35 times at 94° C. for 30 sec, 55° C. for 1 min, and 72° C. for 1 min. The amplified 16S rRNA genes were purified using a commercial kit according to the manufacturer's instructions (QIAquick PCR Purification Kit, Qiagen, Valencia, Calif.) and sequenced on an automated ABI sequencer (Applied Biosystems, Foster City, Calif. The sequencing reactions were initiated with primers HK12, HK13, and HK14 (5'-GTGCCAGCAGYMGCGGT-3') (SEQ ID NO:9, where Y=C or T, M=A or C). The 16S rRNA gene sequence of each isolate was used as the query sequence for a BLAST search (Altschul, et al., *Nucleic Acids Res*. 25:3389–3402 (1997)]) of GenBank® for similar sequences.

A 16S rRNA gene of strain AN12 was sequenced and compared to other 16S rRNA sequences in the GenBank® sequence database. The 16S rRNA gene sequence from strain AN12 was at least 98% similar to the 16S rRNA gene sequences of high G+C Gram positive bacteria belonging to the genus *Rhodococcus*.

Example 2

Identification of Lycopene Cyclases from *Rhodococcus* and *Deinococcus*

The ORF for crtL was identified by conducting BLAST (Basic Local Alignment Search Tool; Altschul et al., *J. Mol. Biol*. 215:403–410 (1993); see also www.ncbi.nlm.nih.gov/BLAST/) searches for similarity to sequences contained in the BLAST "nr" database (comprising all non-redundant (nr) GenBank® CDS translations, sequences derived from the 3-dimensional structure Brookhaven Protein Data Bank, the SWISS-PROT protein sequence database, EMBL, and DDBJ databases). The genomic sequence of *Rhodococcus erythropolis* AN12 was analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Altschul et al., *Nucleic Acid Res*. 25:3389–3402 (1997)) provided by the NCBI.

Results from the BLAST analysis indicated that the lycopene β-cyclase from *Rhodococcus erythropolis* strain AN12 (SEQ ID NOs:1 and 2) shared homology to a putative carotenoid lycopene β-cyclase DR0801 (GenBank® ID AAF10377.1) from *Deinococcus radiodurans* strain R1 (percent identity=31%, percent similarity=45%, E-value 2e-37) and other CrtL-type of lycopene β-cyclases from plants. ORF DR0801 from *Deinococcus radiodurans* strain R1 (SEQ ID NOs:3 and 4) was also retrieved from the database and analyzed for lycopene β-cyclase activity.

Example 3

*Rhodococcus Erythropolis* AN12 Produces Monocyclic Carotenoids

*Rhodococcus erythropolis* strain AN12 is naturally pigmented. The carotenoid pigments in the strain were extracted and analyzed by HPLC. AN12 cells were grown in 100 ml NBYE (0.8% nutrient broth+0.5% yeast extract) at 26° C. overnight with shaking to the stationary phase. Cells were spun down at 4000 g for 15 min, and the cell pellets were resuspended in 10-ml acetone. Carotenoids were extracted into acetone with constant shaking at room temperature. After 1 hour, the cells were spun down at the same condition as above and the supernatant was collected. The extraction was repeated once, and the supernatants of both extractions were combined and dried under nitrogen. The dried material was redissolved in 0.5-ml methanol and insoluble material was removed by centrifugation at 16,000 g for 2 min in an Eppendorf microcentrifuge 5415C (Brinkmann instruments, Inc., Westbury. N.Y.). The extracted sample of 0.1 ml was used for HPLC analysis.

A Beckman System Gold® HPLC with Beckman Gold Nouveau Software (Columbia, Md.) was used for the study. 0.1 ml of the extraction was loaded onto a 125×4 mm RP8 (5 µm particles) column with corresponding guard column (Hewlett-Packard, San Fernando, Calif.). The flow rate was 1 ml/min. The following solvent program was used: 0–11.5 min linear gradient from 40% water/60% methanol to 100% methanol, 11.5–20 min 100% methanol, 20–30 min 40% water/60% methanol. The spectra data were collected by the Beckman photodiode array detector (model 168).

The *Rhodococcus* AN12 showed a major HPLC peak with an elution time of 14.6 min when monitored at 450 nm. The absorption maximum of the major peak was 465 nm. The absorption of the major peak had a round-up shape with the ratio of peak heights % III/II as zero. % III/II describes the fine structure of the spectrum. The peak height of the longest wavelength absorption band was designated as III, that of the middle absorption band as II. The base line was taken as the minimum between the two peaks. A minor peak was also present at an elution time of 15.6 min. The absorption maxima of the minor peak were 435 nm, 458 nm, and 486 nm. The ratio of the absorption peak heights % III/II was 0.45. The spectrum of the major or minor carotenoids was different from the spectrum of β-carotene (449, 474 nm) or β-carotene derivatives such as echinenone (459 nm) or canthaxanthin (474 nm). Instead, the spectrum of the minor peak carotenoid matched well with that of γ-carotene (435–440 nm, 460 nm, 489 nm) and the spectrum of the major peak carotenoid matched well with that of 4-keto-γ-carotene (465 nm). Furthermore, molecular weight of the major and minor carotenoids of AN12 determined by LC/MS as 550 Dalton and 536 Dalton also agrees with the molecular weight of 4-keto-γ-carotene and γ-carotene. These results are consistent with the report about some *Rhodococcus* strains producing γ-carotene-like carotenoids (Ichiyama et al., *Microbiol. Immunol.* 33:503–508 (1989)). Gamma-carotene-like carotenoids contain only one β-ionone ring comparing to two β-ionone rings for β-carotene derivatives. It is likely that the CrtL β-cyclase in AN12 asymmetrically cyclizes only one end of the lycopene substrate to produce γ-carotene-like carotenoids rather than symmetrically cyclizes both ends to produce β-carotene derivatives.

Example 4

Construction of the Lycopene Accumulating *E. Coli* Strain

In order to confirm the monocyclization activity of the *Rhodococcus* lycopeneβ-cyclase CrtL, the *Rhodococcus* crtL gene was expressed in an *E. coli* strain accumulating lycopene (FIG. 2). The lycopene accumulating *E. coli* strain was constructed by transposon insertion into the crtY gene of the *Pantoea* crtEXYIB cluster.

The crtEXYIB cluster was amplified from *Pantoea stewartii* (ATCC 8199) by the following method. Primers were designed using the sequence from *Erwinia uredovora* to amplify a fragment by PCR containing the crf genes. These sequences included:

```
5'-ATGACGGTCTGCGCAAAAAAACACG-3'        (SEQ ID No:5)

5'-GAGAAATTATGTTGTGGATTTGGAATGC-3'     (SEQ ID No:6)
```

Chromosomal DNA was purified from *Pantoea stewartii* (ATCC no. 8199) and Pfu Turbo® polymerase (Stratagene, La Jolla, Calif.) was used in a PCR amplification reaction under the following conditions: an initial period of 94° C. for 5 min, followed by 25 cycles of 94° C. for 1 min, 60° C. for 1 min, and 72° C. for 10 min. Following the last cycle there was an extension period of 72° C. for 10 min. A single product of 6.3 kb was observed following gel electrophoresis. Taq polymerase (Perkin Elmer) was used in a ten minute 72° C. reaction to add additional 3' adenosine nucleotides to the fragment for TOPO® cloning into pCR®4-TOPO® (Invitrogen, Carlsbad, Calif.). Following transformation to *E. coli* DH5α (Life Technologies, Rockville, Md.) by electroporation, several colonies appeared to be bright yellow in color indicating that they were producing a carotenoid compound. The 6.3 kb EcoRI fragment containing the crf gene cluster (crtEXYIB) was cloned into broad-host range vector pBHR1 (MoBiTec, LLC, Marco Island, Fla.) to form pBHR-crt1. The *E. coli* strain with pBHR-crt1 containing the wild type crtEXYIB gene cluster produced β-carotene. The chloramphenicol resistance gene promoter on pBHR1 vector likely directed the functional expression of the crt genes.

In vitro transposon mutagenesis of pBHR-crt1 was performed using EZ::TN™<TET-1> insertion kit (Epicentre Technologies, Madison, Wis.) by following manufacturer's instructions. Insertion mutants of three colors were obtained: white, yellow, and pink. The pink mutants likely had transposon insertion at the crtY gene and as a result accumulated lycopene. The transposon insertion in one of the pink mutant was confirmed by sequencing using the transposon specific primers FP-1 and RP-1 from the EZ::TN™ insertion kit. The plasmid carried this insertion in crtY gene of pBHR-crt1 and was designated as pDCQ51. Plasmid pDCQ51 was transformed into MG1655 *E. coli* strain. The carotenoid content in the strain was analyzed by HPLC as described previously. MG1655 (pDCQ51) cells accumulated lycopene, comparing to β-carotene produced in MG1655 (pBHR-crt1) strain without any transposon insertion. This is consistent with the block of the lycopene cyclization by crtY insertion on pDCQ51. MG1655 (pDCQ51) is subsequently used as a reporter strain for assaying lycopene cyclase activity.

Example 5

Expression of the Lycopene Cyclases in *E. Coli*

The lycopene cyclase genes from *Pantoea stewartii* (ATCC 8199), *Rhodococcus erythropolis* AN12 and *Deinococcus radiodurans* R1 (ATCC 13939) were individually expressed in *E. coli* using the pTrcHis2-TOPO® expression vector (Invitrogen, Carlsbad Calif.). The pTrcHis2 vector for lycopene cyclase expression was compatible with the pBHR1-based reporter plasmid pDCQ51 containing the *Pantoea* crt genes. Function of the *Rhodococcus* CrtL and the homologous *Deinococcus* CrtL (DR0801) was characterized by heterologous expression of these crtL genes in *E. coli* strain accumulating lycopene. The *Rhodococcus* AN12 lycopene cyclase crtL gene was PCR amplified using primers AN12wtY_F (5'-ATGAGCACACTCGACTCCTCC-3') (SEQ ID NO:10) and AN12wtY_R (5'-TCACCG-GAAAAACGGCGC-3')(SEQ ID NO:11). The Deinococcus lycopene cyclase crtL gene was PCR amplified using primers crtY_F(Deino) (5'-ATGGCGCCTTTTTCCCCCGCGA-3')(SEQ ID NO:12) and crtY_R(Deino) (5'-TCAAATCT-TCAGCCCCGCAGCG-3')(SEQ ID NO: 13). The *Pantoea* lycopene cyclase crtY gene was also PCR amplified using primers crtY_F (5'-ATGCAACCGCACTATGATCT-3') (SEQ ID NO:14) and crtY_R (5'-TCAACGATGAGTCGT-CATAATT-3')(SEQ ID NO: 15). The 1149 bp *Pantoea* crtY was cloned in pTrcHis2 expression vector resulting in plasmid pDCQ118 (forward orientation) and pDCQ120 (reverse orientation). The 1131 bp *Rhodococcus* crtL was cloned in pTrcHis2 expression vector resulting in plasmid pDCQ119 (forward orientation) and pDCQ121 (reverse orientation). The 1233 bp *Deinococcus* crtL was cloned in pTrcHis2 expression vector resulting in plasmid pDCQ128 (forward orientation) and pDCQ129 (reverse orientation). All six plasmids were confirmed by restriction analysis and sequencing. They were subsequently electroporated into the lycopene producing MG1655(pDCQ51) cells. Transformants of the clones containing cyclase genes in reverse orientation were pink as the MG1655(pDCQ51) host cells, indicating that lycopene substrate was still present in these cells. Transformants of the clones containing cyclase genes in forward orientation were no longer pink, suggesting that the lycopene substrate was converted to products by the expressed lycopene cyclases. Interestingly, transformants of pDCQ119 (*Rhodococcus* crtL) and pDCQ128 (*Deinococcus* crtL) showed orange color different from the yellow transformants of pDCQ118 (*Pantoea* crtY), suggesting that *Rhodococcus* or *Deinococcus* CrtL produced different carotenoids from the lycopene substrate as the β-carotene produced by *Pantoea* CrtY.

Example 6

Analysis of the Carotenoids Produced from the *E. Coli* Strains Expressing Lycopene Cyclases The carotenoids produced from the above six *E. coli* strains expressing different lycopene β-cyclases were analyzed by HPLC (Table 1). Individual strains were grown in 50 ml LB medium with 100 µg/ml ampicillin and 25 µg/ml kanamycin at 37° C. overnight. Cells were harvested at 4000 g for 15 min and the pellet was resuspended in 10 ml acetone. Carotenoids were extracted into acetone with constant shaking at room temperature for 1 hour. The cells were spun down and the extraction was repeated once. The acetone extracts from both extractions were combined and dried under nitrogen. The dried material was re-dissolved in 1 ml methanol and insoluble material was removed by passing through a 0.2 µm Acrodisc® HPLC certified syringe filter (Gelman-Pall Life Sciences, Ann Arbor, Mich.). The filtered sample of 0.1 ml was used for HPLC analysis using the same method as described in Example 1.

Figure 3:
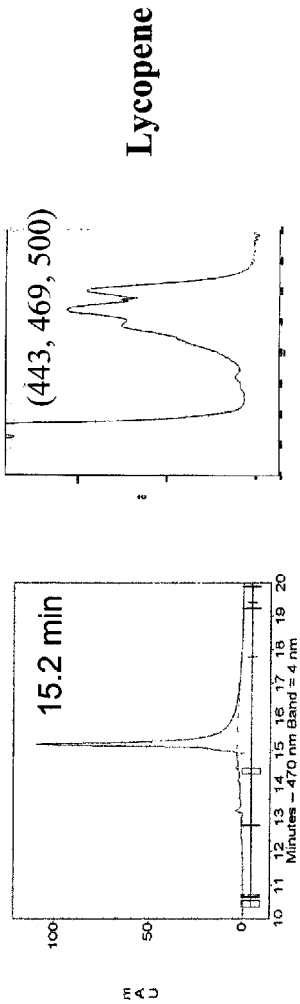
FIG. 3 illustrates the HPLC elution profiles and absorption spectra of the carotenoids from the MG1655(pDCQ51) alone and those with the *Rhodococcus* CrtL or *Pantoea* CrtY expression.
Figure 3:
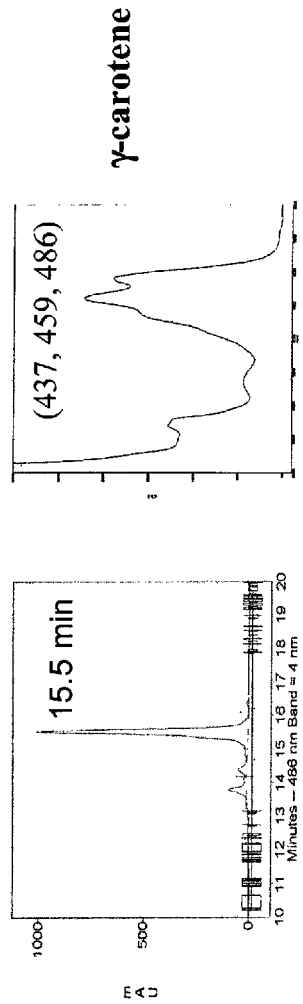
Figure 3:
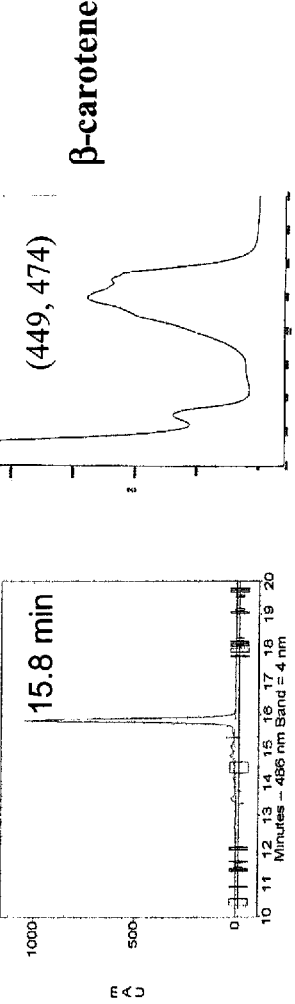
Figure 4:
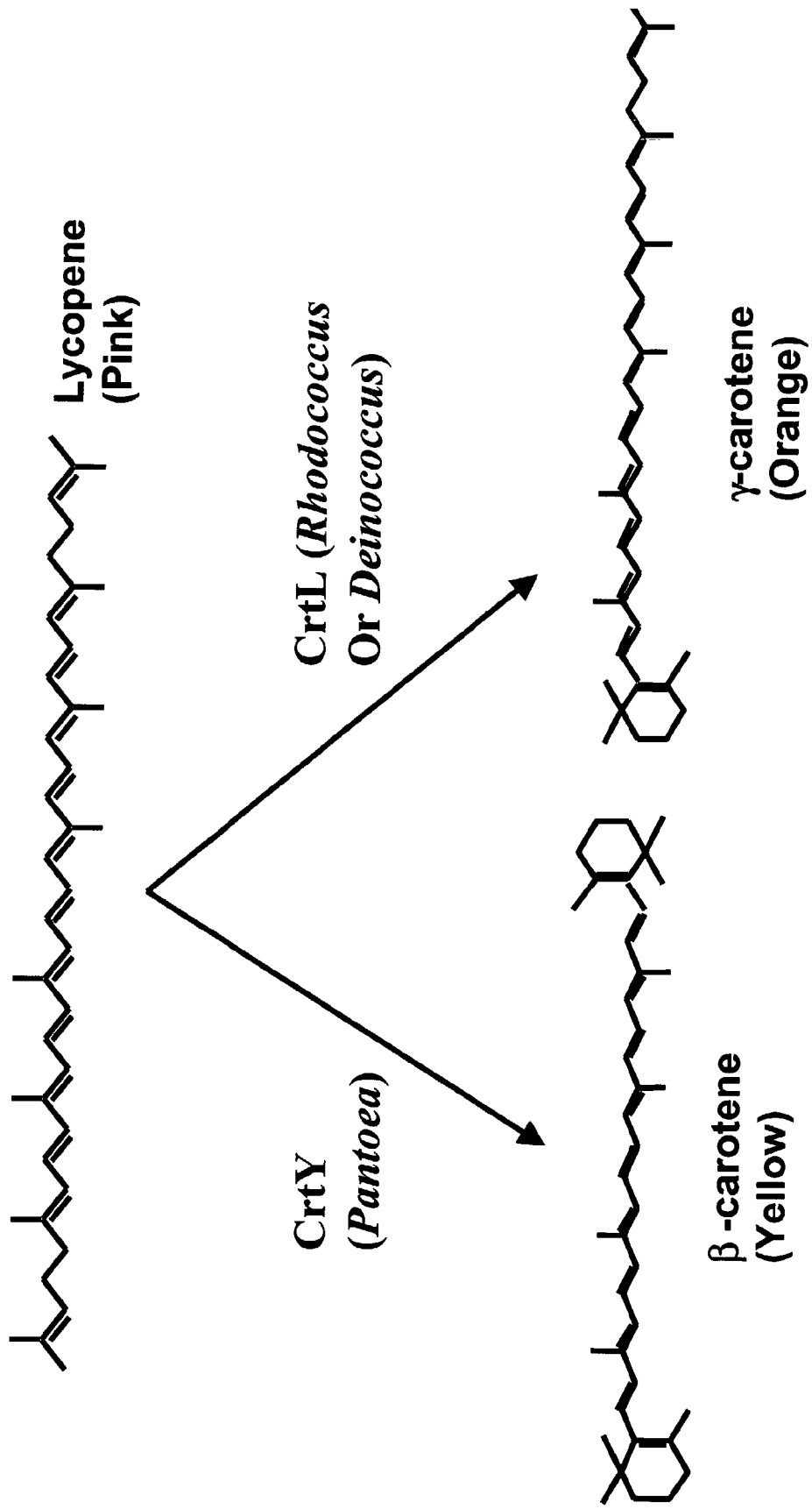
FIG. 4 illustrates the different enzymatic reactions catalyzed by the *Pantoea* lycopene β-cyclase CrtY and the *Rhodococcus* or *Deinococcus* lycopene β-cyclase CrtL using the same acyclic substrate, lycopene.

The carotenoids extracted from the pink strains containing pDCQ51 alone or with additional lycopene β-cyclases cloned in reverse orientation produced a carotenoid with the same elution time, absorption spectrum as the authentic standard of lycopene compound from Sigma (St Louis, Mo.). The carotenoid extracted from the yellow strain with pDCQ118 containing *Pantoea* crtY in forward orientation produced a carotenoid matched with the authentic standard of β-carotene (FIG. 3). This confirmed the function of CrtY as lycopene β-cyclase to convert lycopene to β-carotene, which validated the in vivo complementation assay system with pDCQ151 lycopene producing plasmid and pTrcHis2-based cyclase expression plasmid. The carotenoids extracted from the orange strains containing lycopene cyclase crtL either from *Rhodococcus* (pDCQ119) or *Deinococcus* (pDCQ128) produced a different carotenoid from lycopene or 1-carotene. The retention time (15.5 min) and the absorption spectra (437 nm, 459 nm, 486 nm) of this peak matched well with those of the minor peak carotenoid of the *Rhodococcus erythropolis* AN12, which is likely to be γ-carotene (Example 1). No β-carotene was detected in these two CrtL-expressing strains containing pDCQ119 or pDCQ128. These data suggested that lycopene β-cyclase CrtL from *Rhodococcus* or *Deinococcus*, unlike the *Pantoea* CrtY, converted lycopene to monocyclic γ-carotene (FIG. 4). The monocyclization activity of CrtL may also explain why *Rhodococcus erythropolis* AN12 produces carotenoids of γ-carotene derivatives.

TABLE 1

Phenotypes of the lycopene β-cyclase expression in MG1655(pDCQ51) and HPLC analysis of the major carotenoid in the expression clones.

| Expression plasmid | Cloned gene(orientation) | Colony Color | HPLC elution time | Absorption Spectrum | Carotenoid identified |
|---|---|---|---|---|---|
| pDCQ118 | Pantoea crtY(F) | Yellow | 15.8 min | 449, 474 nm | β-carotene |
| pDCQ119 | Rhodococcus crtL(F) | Orange | 15.5 min | 437, 459, 486 nm | γ-carotene |
| pDCQ128 | Deinococcus crtL(F) | Orange | 15.5 min | 437, 459, 486 nm | γ-carotene |
| pDCQ120 | Pantoea crtY(R) | Pink | 15.3 min | 443, 469, 500 nm | lycopene |
| pDCQ121 | Rhodococcus crtL(R) | Pink | 15.2 min | 443, 469, 500 nm | lycopene |
| pDCQ129 | Deinococcus crtL(R) | Pink | 15.2 min | 443, 469, 500 nm | lycopene |
| Host only | No crtY/L | Pink | 15.3 min | 443, 469, 500 nm | lycopene |
| standard | Lycopene | NA | 15.2 min | 443, 469, 500 nm | lycopene |
| standard | β-carotene | NA | 15.8 min | 449, 474 nm | β-carotene |

What is claimed is:

1. A method for the production of γ carotene or 4-keto-γ-carotene comprising:

a) providing a host cell which produces lycopene or neurosporene wherein said host cell expresses a lycopene β-cyclase that converts lycopene or neurosporene into γ-carotene or 4-keto-γ-carotene and is encoded by a nucleic acid molecule selected from the group consisting of:

(i) an isolated nucleic acid molecule encoding the amino acid sequence of SEQ ID NO:2; and;

(ii) an isolated nucleic acid molecule that hybridizes with (i) under the following hybridization conditions: 0.1×SSC, 0.1% SDS, 65° C. and washed with 2×SSC, 0.1% SDS followed by 0.1×SSC, 0.1% SDS;

b) growing the host cell of (a) under conditions whereby γ-carotene or 4-keto-γ-carotene are produced; and c) Optionally recovering the γ-carotene or 4-keto-γ-carotene.

* * * * *

SEQUENCE LISTING

<160> NUMBER OF SEQ ID NOS: 13

<210> SEQ ID NO 1
<211> LENGTH: 1131
<212> TYPE: DNA
<213> ORGANISM: Rhodococcus erythropolis AN12

<400> SEQUENCE: 1

```
atgagcacac tcgactcctc cgccgacgtg gtgatcgtgg gcggagggcc ggcggggcgg     60
gcactcgcga cgcgctgtat cgcccggcaa ctcactgttg tcgttgtcga tccgcatcct    120
catcgggtgt ggacgccgac gtactcggtg tgggcagacg agctgccgtc gtggctgccg    180
gacgaggtga tcgcgagccg aatcgaacgc ccgagcgtgt ggaccagcgg gcagaaaacg    240
cttgatcgca tctattgcgt attgaataca tctttactgc aatcatttct ctcccacaca    300
tccataaagg tcagaggctt acgcgctcaa acactgtcca ccaccacgt cgtgtgcgtg    360
gacggatcgc agctgacggg atccgtcgtc gtcgacgccc gaggcaccga tctggcagtg    420
acaaccgcgc agcagacggc cttcggaatg atcgtggacc gagctctggc cgatccgatt    480
ctgggcggca gcgaggcctg gttcatggac tgcgaacag acaacggcac ctccgacgcc    540
gacactccgt cgtttctcta cgcggtcccg ctcgacgacg agcgagtcct cctcgaggag    600
acctgcctcg tcggccggcc ggcgttgggg ttgcgtgaac tcgaaacacg tctgcgcacc    660
cgacttcaca atcggggctg cgaagtcccc gacgacgcgc cggtcgagcg agtccgtttt    720
gcggtcgaag gcccgaggga ctcgtccccg gacggtgtcc tccggttcgg cgggcgaggc    780
ggtctgatgc atccgggaac cggatacagc gttgcctcct cactcgccga ggccgacact    840
gtcgcgaaag caatcgccga cggtgaggat ccgaacgcgg cactctggcc tcgctcggcc    900
aaggcggtat ccgctctccg ccgcgttggt ctgaacgcac ttctcaccct cgactcgggc    960
gaagtcacca cattcttcga caagttcttc gatctaccgg tcgaggctca gcggtcatac   1020
cttttccgatc ggcgggacgc ggccgcgacg gcgaaggtga tggcaacact gttccgatcg   1080
tcaccgtggc acgtcagaaa gacgttgatg cgcgcgccgt ttttccggtg a            1131
```

<210> SEQ ID NO 2
<211> LENGTH: 1233
<212> TYPE: DNA
<213> ORGANISM: Deinococcus radiodurans R1

<400> SEQUENCE: 2

```
atggcgcctt tttccccgc gagttccgac gtgctggtca tcggcggcgg cccgagcggc     60
accgccctga gcgccgaact cgccgcgcgg ggactggacg tgcagcagct cgcaccgcat    120
ccaccccggc cttttcccgc cacctacggg gcctggctcg gcgacctgcc cacctgggcg    180
cgaggctgcg cggagcaggt ctggaccgac gtgcgcgcgt acaccggtcc ccagcccaca    240
tcgctggggc agccttatgc gctgctcgac aacgccgcgt gctgcggac cctgcgcggg    300
cttgccgact ggacctgggt ggaaggagcc gccctgcacg ccgagcgcag cggcgcaggc    360
tggaccgtgt acggcgcggg cggcgagcgt tggcagaccc ggctggtcgt ggacgccagt    420
gggcatgggg cgctcgtgtc tccggtccgg tttccggtg gcgcggcgtt gcagacggcc    480
tacggggtgg tggcccgctt tcgccgcccg ccgtcacac ccggcagcat ggtgtggatg    540
gactaccgca cgcccgcgcc ggagctgaag cggggcgagg cgacctttct ctacgccatg    600
cacctcggcg gggaccgcta tttcgtggag gaaacgagcc tgattgcccg gcctgctccg    660
```

```
acccgcgccg agttgcggcg gcggctgctc gcccggctga gcgcccaggg cacaccgccc      720
cacgccaccg agagcgagga atgggtggcc tttcccatga atgcccaggc ccccgcgcct      780
ggcggcgtgc tcgcttacgg cgcggcggcg ggccgggtcc atccggtgag cggttttcag      840
gtggccgggg cactcagtga cgcgccggga gtggccaccg ccattgccac agcccttttgc     900 cagggtaaag acgccgccgc cgctggctgg gccgccctgt ggtccccgga gcgacgcgcc      960
gcccgcgagg tgcatctgct cggcgtgggg gcgctgctgg ggctggaacg ggccgagctg     1020
ccgcattttt tcggcacctt cttcggcctg ccgcgcgagc agtgggcgcg tttcctgcac     1080
cccgacaccg acgcgggcac cctggcgcgg accatgctgc gggtgttcgc gcagacgggg     1140
ggccgggtac gcctgccgct cgccgtgccc gccctcgcgc agcccgccgc gagtggccgg     1200
gcactggccg ccgctgcggg gctgaagatt tga                                 1233
```

<210> SEQ ID NO 3
<211> LENGTH: 25
<212> TYPE: DNA
<213> ORGANISM: artificial sequence
<220> FEATURE:
<223> OTHER INFORMATION: Primer1forPCRofcrtEXYIB is a primer useful for
      amplifying the crt EXYIB gene cluster from Pantoea stewartii
      (ATCC 8199).

<400> SEQUENCE: 3
atgacggtct gcgcaaaaaa acacg                                            25

<210> SEQ ID NO 4
<211> LENGTH: 28
<212> TYPE: DNA
<213> ORGANISM: artificial sequence
<220> FEATURE:
<223> OTHER INFORMATION: Primer2forPCRofcrtEXYIB is a primer useful for
      amplifying the crt
      EXYIB gene cluster from Pantoea stewartii (ATCC 8199).

<400> SEQUENCE: 4
gagaaattat gttgtggatt tggaatgc                                         28

<210> SEQ ID NO 5
<211> LENGTH: 19
<212> TYPE: DNA
<213> ORGANISM: artificial sequence
<220> FEATURE:
<223> OTHER INFORMATION: Primer HK12 is a primer using for amplifying
      and/or sequencing the 16s rRNA from Rhodococcus erythropolis
      strain AN12.

<400> SEQUENCE: 5
gagtttgatc ctggctcag                                                   19

<210> SEQ ID NO 6
<211> LENGTH: 16
<212> TYPE: DNA
<213> ORGANISM: artificial sequence
<220> FEATURE:
<223> OTHER INFORMATION: Primer HK13 is a primer using for amplifying
      and/or sequencing the 16s rRNA from Rhodococcus erythropolis
      strain AN12.

<400> SEQUENCE: 6
taccttgtta cgactt                                                      16

<210> SEQ ID NO 7

```
<211> LENGTH: 17
<212> TYPE: DNA
<213> ORGANISM: artificial sequence
<220> FEATURE:
<223> OTHER INFORMATION: Primer HK14 is a primer using for amplifying
      and/or sequencing the 16s rRNA from Rhodococcus erythropolis
      strain AN12.

<400> SEQUENCE: 7
gtgccagcag ymgcggt                                                  17

<210> SEQ ID NO 8
<211> LENGTH: 21
<212> TYPE: DNA
<213> ORGANISM: artificial sequence
<220> FEATURE:
<223> OTHER INFORMATION: Primer AN12wtY-F is a primer useful for
      amplifying the crtL gene from Rhodococcus erythropolis strain
      AN12.

<400> SEQUENCE: 8
atgagcacac tcgactcctc c                                             21

<210> SEQ ID NO 9
<211> LENGTH: 18
<212> TYPE: DNA
<213> ORGANISM: artificial sequence
<220> FEATURE:
<223> OTHER INFORMATION: Primer AN12wtY-R is a primer useful for
      amplifying the crtL gene from Rhodococcus erythropolis strain
      AN12.

<400> SEQUENCE: 9
tcaccggaaa aacggcgc                                                 18

<210> SEQ ID NO 10
<211> LENGTH: 22
<212> TYPE: DNA
<213> ORGANISM: artificial sequence
<220> FEATURE:
<223> OTHER INFORMATION: Primer crtY_F(Deino) is a primer useful for
      amplifying the crtL gene from Deinococcus radiodurans strain R1
      (ATCC 13939).

<400> SEQUENCE: 10
atggcgcctt tttcccccgc ga                                            22

<210> SEQ ID NO 11
<211> LENGTH: 22
<212> TYPE: DNA
<213> ORGANISM: artificial sequence
<220> FEATURE:
<223> OTHER INFORMATION: Primer crtY_R(Deino) is a primer useful for
      amplifying the crtL gene from Deinococcus radiodurans strain R1
      (ATCC 13939).

<400> SEQUENCE: 11
tcaaatcttc agccccgcag cg                                            22

<210> SEQ ID NO 12
<211> LENGTH: 20
<212> TYPE: DNA
<213> ORGANISM: artificial sequence
<220> FEATURE:
<223> OTHER INFORMATION: Primer crtY_F is a primer useful for amplifying
      the crtY gene from Pantoea stewartii (ATCC 8199).

<400> SEQUENCE: 12
```

```
atgcaaccgc actatgatct                                          20
```

<210> SEQ ID NO 13
<211> LENGTH: 22
<212> TYPE: DNA
<213> ORGANISM: artificial sequence
<220> FEATURE:
<223> OTHER INFORMATION: Primer crtY_R is a primer useful for amplifying
      the crtY gene from Pantoea stewartii (ATCC 8199).

<400> SEQUENCE: 13

```
tcaacgatga gtcgtcataa tt                                       22
```